(12) United States Patent
Braile et al.

(10) Patent No.: US 11,471,278 B2
(45) Date of Patent: Oct. 18, 2022

(54) VALVED ENDOPROSTHESIS RELEASING DEVICE AND VALVED ENDOPROSTHESIS

(71) Applicant: BRAILE BIOMÉDICA INDÚSTRIA, COMÉRCIO E REPRESENTAÇÕES SA, São Jose do Rio Preto (BR)

(72) Inventors: Domingo Marcolino Braile, São José do Rio Preto (BR); Rafael Braile Cunha, São José do Rio Preto (BR); Diego Felipe Gaia Dos Santos, São Paulo (BR); José Honório De Almeida Palma De Fonseca, São Paulo (BR); Lucas Monteiro Cardoso, São José do Rio Preto (BR); Gláucia Grazielli Basso Frazzato, São José do Rio Preto (BR); Ana Luiza Pereira Da Silva Tozzetti, São José do Rio Preto (BR)

(73) Assignee: BRAILE BIOMÉDICA INDÚSTRIA, COMÉRCIO E REPRESENTAÇ, São José do Rio Preto (BR)

(*) Notice: Subject to any disclaimer, the term of this patent is extended or adjusted under 35 U.S.C. 154(b) by 0 days.

(21) Appl. No.: 16/610,809

(22) PCT Filed: Apr. 27, 2018

(86) PCT No.: PCT/BR2018/050137
§ 371 (c)(1),
(2) Date: Nov. 4, 2019

(87) PCT Pub. No.: WO2018/201212
PCT Pub. Date: Nov. 8, 2018

(65) Prior Publication Data
US 2021/0154008 A1    May 27, 2021

(30) Foreign Application Priority Data

May 2, 2017 (BR) .......................... 102017009222-4

(51) Int. Cl.
*A61F 2/24* (2006.01)
*A61F 2/966* (2013.01)

(52) U.S. Cl.
CPC .......... *A61F 2/2433* (2013.01); *A61F 2/2418* (2013.01); *A61F 2/2436* (2013.01);
(Continued)

(58) Field of Classification Search
CPC ........ A61F 2/24; A61F 2/2418; A61F 2/2409; A61F 2250/0039; A61F 2/2433; A61F 2/07
See application file for complete search history.

(56) References Cited

U.S. PATENT DOCUMENTS 8,940,040 B2 *   1/2015   Shahriari ................ A61F 2/962
                                                            623/1.35
9,119,716 B2 *   9/2015   Lee ....................... A61F 2/2433
(Continued)

*Primary Examiner* — Brian A Dukert
(74) *Attorney, Agent, or Firm* — Andrew S. Rapacke

(57) ABSTRACT

A valved endoprosthesis releasing device and a valved endoprosthesis pertaining to the medicine area, more particularly a device for releasing valved endoprosthesis specifically developed for the combined endovascular treatment of aortic valve disease and ascending aorta segment, said device allowing the assembly to travel endovascularly until the valved endoprosthesis is specifically coupled to repair injured segments of the ascending aorta and replace the calcified aortic valve, besides restoring the anatomy and assuring the consolidation of a suitable blood flow in the region to be treated. The invention comprises a valved endoprosthesis releasing device consisting of several overlapped tubular segments, wherein the movement of the sheath tube releases the valved endoprosthesis coupled to the proximal region for endovascular implantation by expanding the balloon or self-expanding a valved endoprosthesis provided with a tubular body coupled to an aortic valve.

4 Claims, 33 Drawing Sheets

(52) U.S. Cl.
CPC ...... *A61F 2/966* (2013.01); *A61F 2002/9665* (2013.01); *A61F 2220/0075* (2013.01); *A61F 2250/0098* (2013.01)

(56) References Cited

U.S. PATENT DOCUMENTS 9,717,592 B2 * 8/2017 Thapliyal ................. D04C 1/08
9,744,032 B2 * 8/2017 Roeder ................. A61F 2/2412

* cited by examiner

Det. C

Det. E

Det. H

Det. L

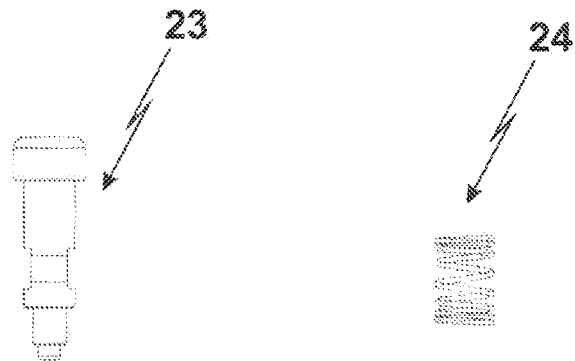
Fig. 41  Fig. 42
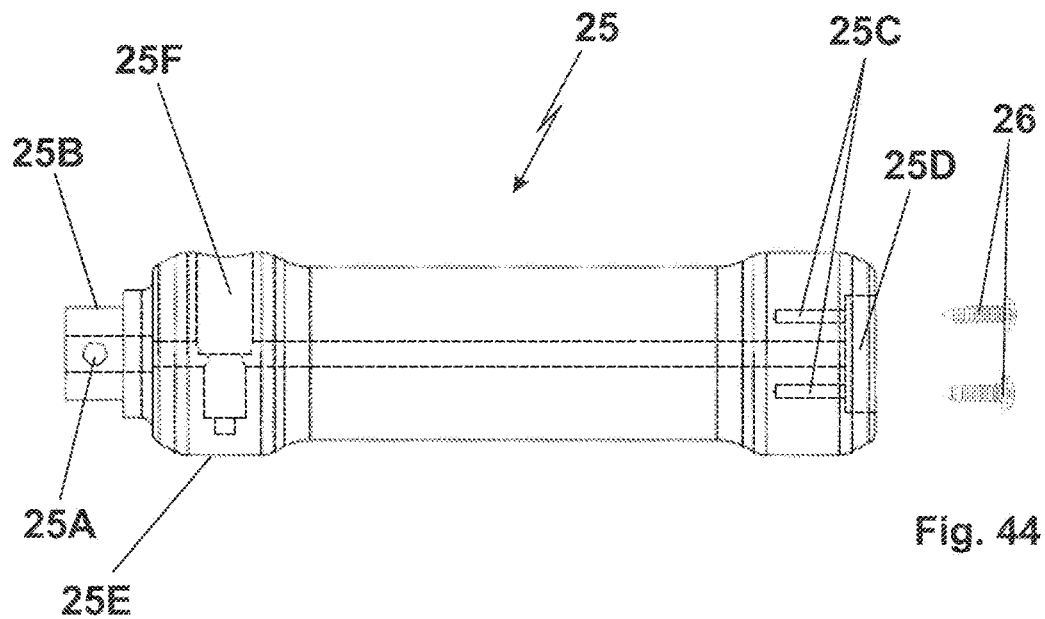
Fig. 43
Fig. 44

VALVED ENDOPROSTHESIS RELEASING DEVICE AND VALVED ENDOPROSTHESIS

FIELD OF THE INVENTION

The present invention provides a valved endoprosthesis releasing device and a valved endoprosthesis pertaining to the medicine area, more particularly a valved endoprosthesis releasing device specifically developed for the combined endovascular treatment of aortic valve disease and ascending aorta segment, said device allowing the assembly to travel endovascularly until the valved endoprosthesis is specifically coupled to repair injured segments of the ascending aorta and replace the calcified aortic valve, besides restoring the anatomy and assuring the consolidation of a suitable blood flow in the region to be treated.

The innovation of this procedure in the sector is related to the fact that it provides the fully endovascular treatment of injuries in the region of the aorta root and the replacement of the aortic valve, besides making it possible to treat effectively and efficiently patients suffering co-morbidities that cannot be treated by the conventional open chest surgical procedure, the so-called Bentall De Bono surgery.

STATE OF THE ART

Aorta related diseases have a high morbimortalily and are treated adequately only when the diagnosis is given at an early time. The degenerative ascending aorta diseases, as well as the handling of the aorta root and the aortic valve, are objects of discussion and several recent contributions in the relevant literature. The rupture of an aortic aneurism, for example, causes severe hemorrhage and high risk of mortality[1].

In the present state of the art, the usual technique for the surgical treatment of aneurisms and dissections of ascending aorta with unrecoverable stenosis of the aortic valve was established by Bentall & De Bono in 1968[2]. It comprises usisng a valved tube which makes it possible to correct ascending aorta injuries and replace the aortic valve by reimplanting ostia of the coronary arteries (also known as Bentall De Bono procedure), however, in some cases, the predicted surgical risk associated to the health diagnosis and age can justify the contraindication, due to the fact that the mortality risk is very high[3,4].

Thus, when Bentall and De Bono have proposed to replace the aortic valve and the ascending aorta with a valved tube containing reimplanted coronary ostia in the tube, they have attained great advantages at the time, such as the exclusion of the whole sick aortic segment and the reduction of bleeding[6].

However, inconveniences of said technique have been cited in the literature, namely: intra-operatory bleeding at the level of the coronary ostia[7,8] and late pseudo-aneurisms at the same site[9]. Such complications are probably due to the stress on the aorta wall at the level of the ostia or incomplete ressection of the sick wall.

Besides such factors, the conventional surgical repair method is usually followed by a significant morbidity and high mortality[3,4]. Even when intra-operatory neurological protection methods are used, such procedures are associated to a high incidence of paraplegia (6 to 11%) and encefalic vascular accident (3 to 19%)[10].

Thus, in recent years, the concept that aorta related diseases could be corrected by endovascular prostheses located inside the aorta by using catheters has risen. Considering the high morbimortalily rate related to surgical interventions in dissections and toraxic aneurisms, the endovascular technique has become a very attractive option[5].

Similarly, in the case where the aortic valve is treated, an aortic valve is implanted under the degenerated valve where the valve to be implanted valve is conveyed through a catheter towards the target and probably expanded with the aid of a balloon at the site.

In this respect, attention should be drawn to document BR 102014007735-9 A2, published on Dec. 8, 2015, whose applicants are Melchiades da Cunha Neto and Alexander Marra Moreira and is directed to a "Percutaneous aortic valve device assembled on an expandable endoprosthesis which, according to its abstract, promotes the treatment of vascular diseases, notably in the case of specific pathologies such as aneurisms and aorta dissections, among others, wherein said device is referred to as an aortic valve to be implanted through a catheter into the sick native aortic valve of the patient being treated, said device is comprised of a metallic structure to which follicles of biologic/polymeric material are sutured and wherein an inner sealing layer also made of polymeric/biologic material is defined, and said device is particularly installed at the site to be treated with a releasing catheter having releasing controls." It can be seen that this invention only comprises an aortic valve to be implanted by a catheter and is restricted to the treatment of the aortic valve, but cannot be used in the combined endovascular treatment of aortic valve related diseases and ascending aorta segment. Therefore, it is a device that is limited and restricted to the treatment of aortic valve.

Another document that deserves attention is patent PI0612476-3 A2, entitled "KIT DESIGNED TO BE IMPLANTED INTO A BLOOD CIRCULATION CONDUIT, A TUBULAR ENDOPROSTHESIS AND A PROSTHETIC VALVE", published on Nov. 23, 2010, filed by Laboratoires Perouse, which patent, according to its abstract, "refers to a kit (11) that comprises a tubular endoprosthesis (19) having an inner surface (57) that delimits a channel (58) having a longitudinal axis (X-X). It comprises a valve (17) having a bearing structure (25) provided with an outer surface (35A, 35B) to be applied against the inner surface (57), and a flexible obturator (39) connected to the structure (25). The inner surface (57) has at least two segments (65, 67) having a variable cross-section along the longitudinal axis (X-X). The segments (65, 67) form a proximal stop (71) and a distal stop, respectively, (73) to prevent the outer surface (35A, 35B) from moving axially along the inner surface (57) in two opposite directions." It should be pointed out that the cited patent does not provide the treatment of ascending aorta, besides the fact that the valve is placed in the center of the device and not at the proximal end thereof, which is the innovation presented in this inventive solution. In addition, the device presented in patent "PI0612476-3 A2" does not satisfy the requirements concerning the combined endovascular treatment of aortic valve disease and ascending aorta segment.

From the state of the art, it can be noticed that there is not any valved endoprosthesis device that is able to carry out the combined treatment of endovascular valve diseases and ascending aorta segment.

It is also noticed that only with the knowledge of the state of the art it is not possible to solve the above cited problem of combined treatment of endovascular valve diseases and ascending aorta segment, since the existing devices, aortic valve and endoprostheses, only allow for the limited treatment of one or the other. For implantations of endoprostheses, proximal and distal regions for anchoring the prosthesis to the wall of the artery are required, however in aorta root aneurisms there is no site for a proximal anchoring since the region ends in the aortic valve, and also there is no way to release the endoprosthesis and keep same in its place, besides the fact that it does not treat aortic valve related problems. The use of only a transcatheter valve makes it possible to treat the cardiac valve disfunction, but cannot treat aorta root problems.

OBJECTS OF THE INVENTION

In view of the limitations of conventional systems for the surgical repair of aortic arc through thoracotomy, the object of the present invention is to provide the combined endovascular treatment of aortic valve disease and ascending aorta segment using a valved endoprosthesis releasing device and the valved endoprosthesis itself (graft stent endoprosthesis and transcatheter valve assembly) connected at the proximal region, thus allowing for the fast percutaneous implantation of the prosthesis and treatment of injuries in the ascending aortic portion as well as replacement of the valve, thus perfectly translating the adaptations related to the morphology of the vessels thanks to the flexibility thereof, and it can be implanted safely without damaging the native vessel, and also adapted to patients having more tortuous vessels.

Another object of the present invention is related to the fact that the device can be made according to the anatomical characteristics of the patient and provided with markings at the ends thereof that indicate the correct release side which, depending on the clinical conditions of the patient, make it possible to modify the sides and select the most convenient access way for the adequate treatment of the disease.

Thus, it can be concluded that the valved endoprosthesis releasing device and valved endoprosthesis objects of the present invention are provided with novelty, and are both innovative and functional products, since this invention provides an alternative to the methods for treating patients suffering from ascending aorta diseases, such as aneurisms and dissections, with unrecoverable stenosis of the aortic valve, and said innovation is not obvious compared to the current state of the art and with industrial applicability.

BRIEF DESCRIPTION OF THE INVENTION

The invention comprises a valved endoprosthesis releasing device comprised of a catheter releasing system and valved endoprosthesis coupled to the proximal region for endovascular implantation through the expansion of a balloon or by self-expanding a valved endoprosthesis provided with a tubular body connected to an aortic valve.

DESCRIPTION OF THE FIGURES

The present patent will be better understood through the accompanying drawings that represent schematically a preferred but not limitative embodiment of the device, as follows:

FIG. 41: a side view of the locking pin;
FIG. 42: a side view of the pressure spring;
FIG. 43: a side view of handle;
FIG. 44: a side view of the screws.

DETAILED DESCRIPTION OF THE INVENTION

Figure 1:
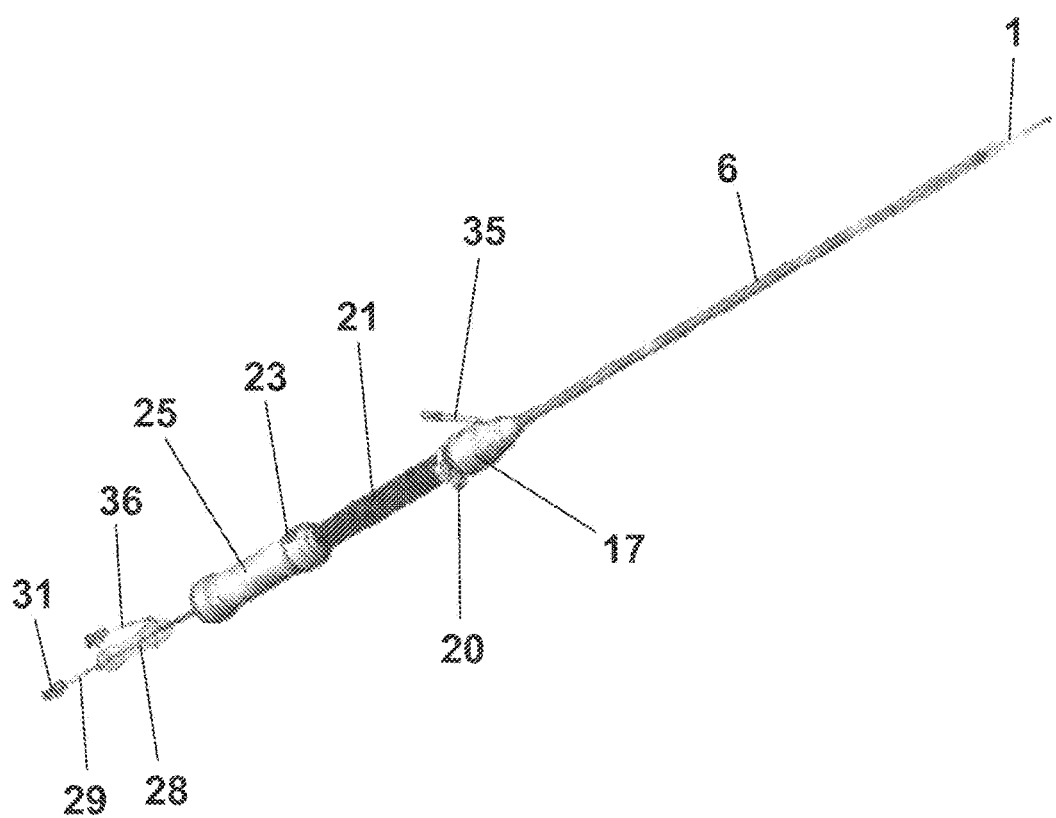
FIG. 1: a perspective view of the valved endoprosthesis releasing device.
Figure 2:
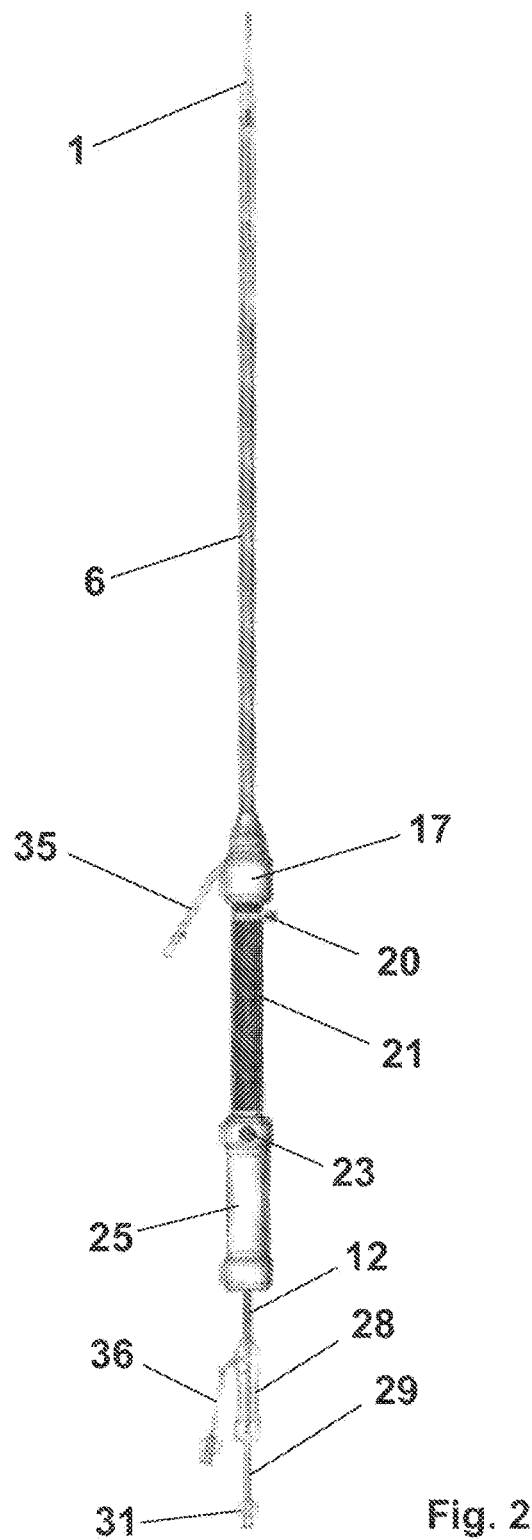
FIG. 2: a side view of the valved endoprosthesis releasing device.
Figure 3:
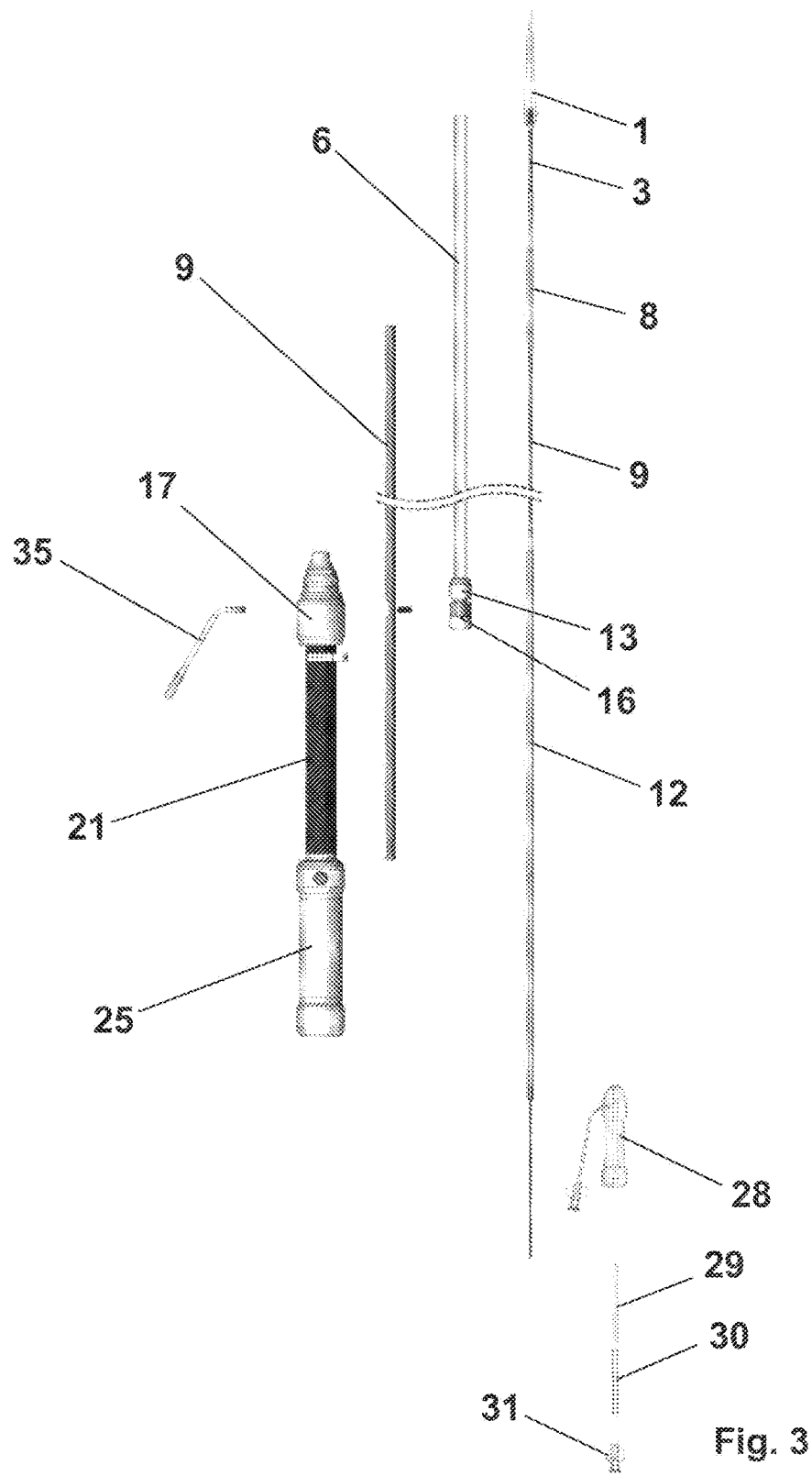
FIG. 3: a partially exploded side view of the valved endoprosthesis releasing device.
Figure 4:
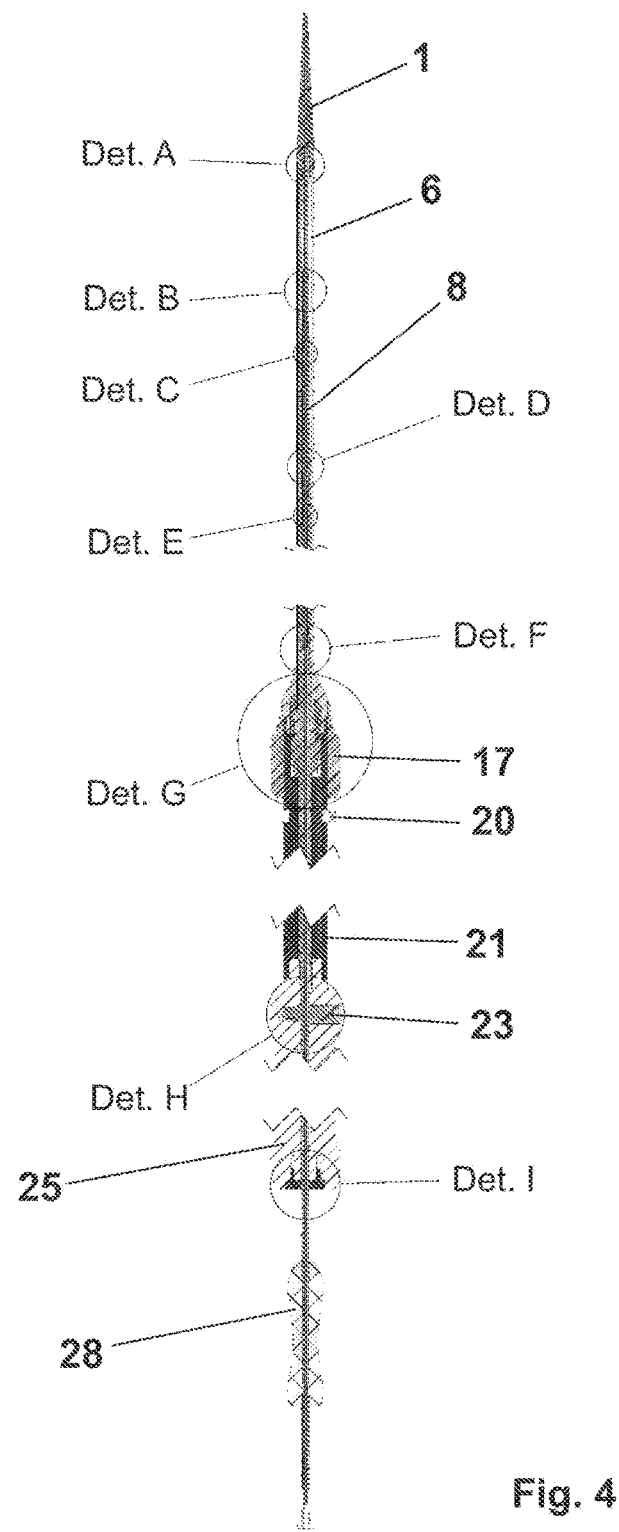
FIG. 4: a cut top view of the valved endoprosthesis releasing device.
Figure 5:
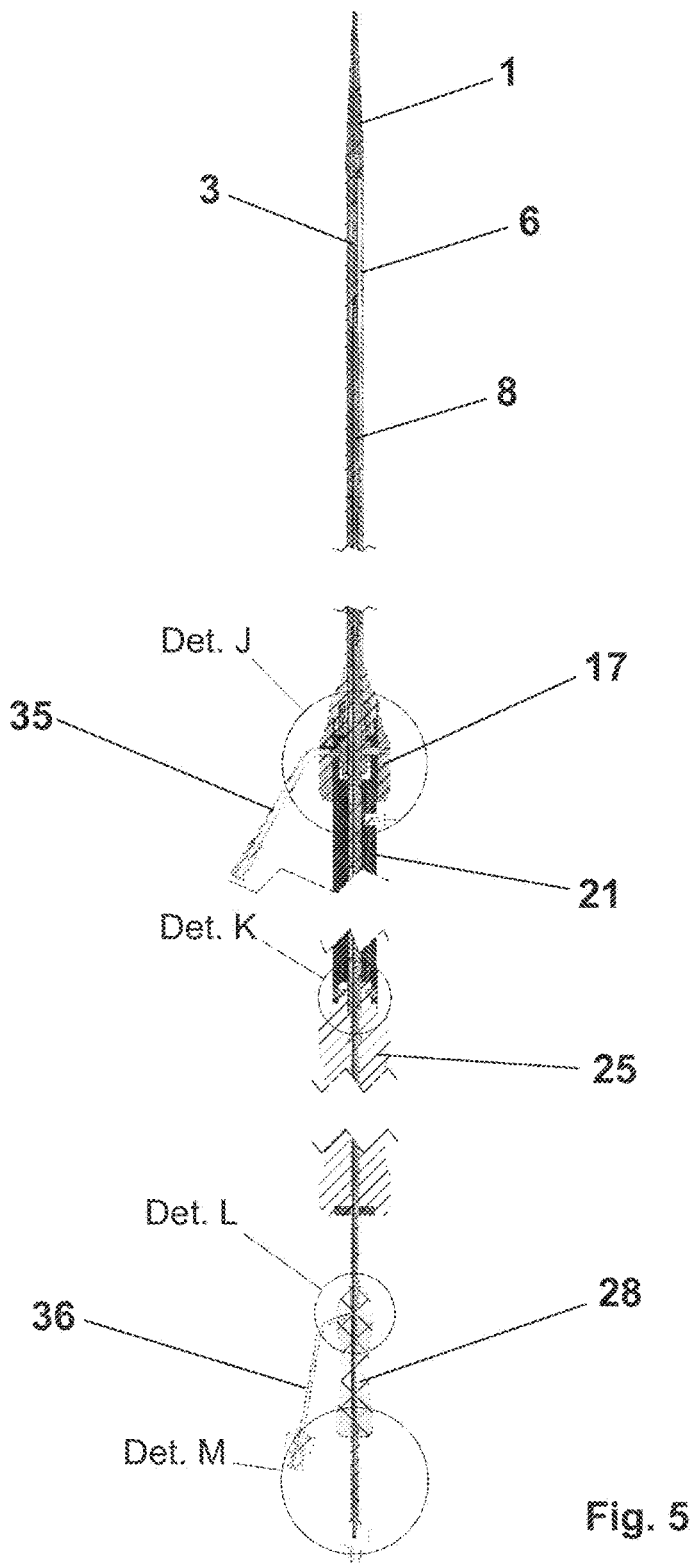
FIG. 5: a cut side view of the valved endoprosthesis releasing device.
Figure 6:
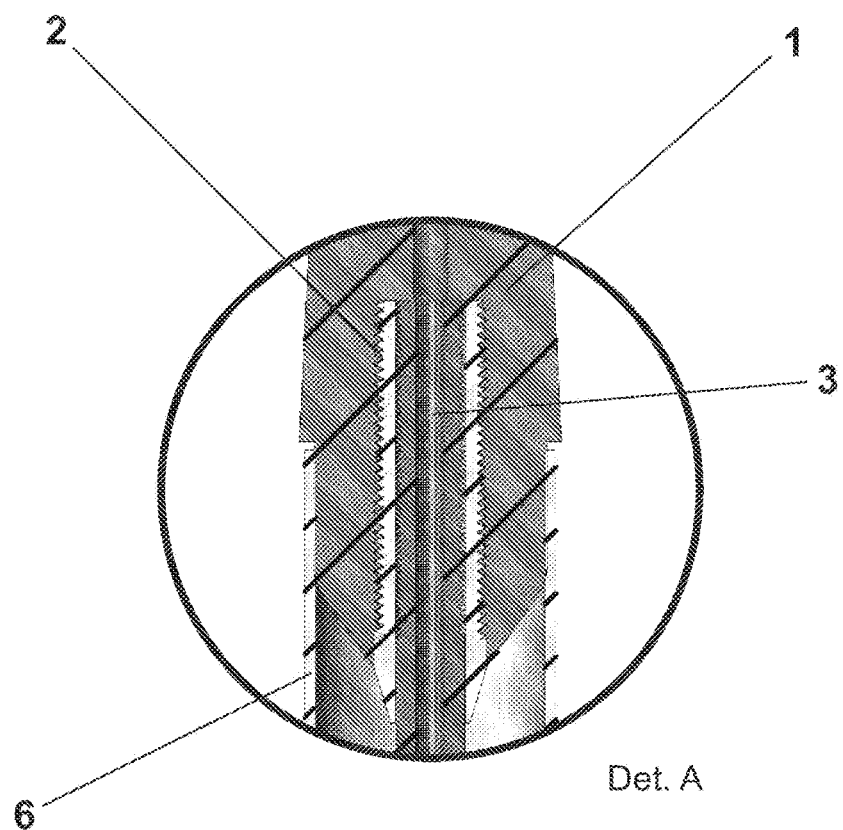
FIG. 6: detail A indicated in FIG. 4.
Figure 7:
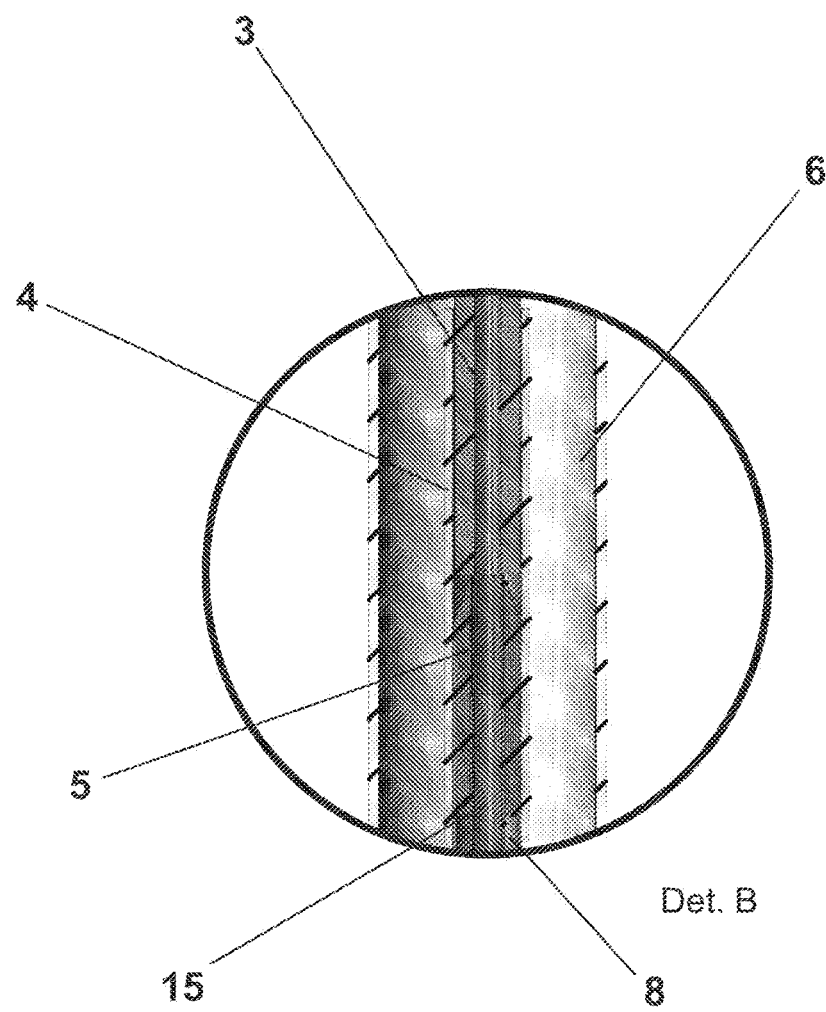
FIG. 7: detail B indicated in FIG. 4.
Figure 8:
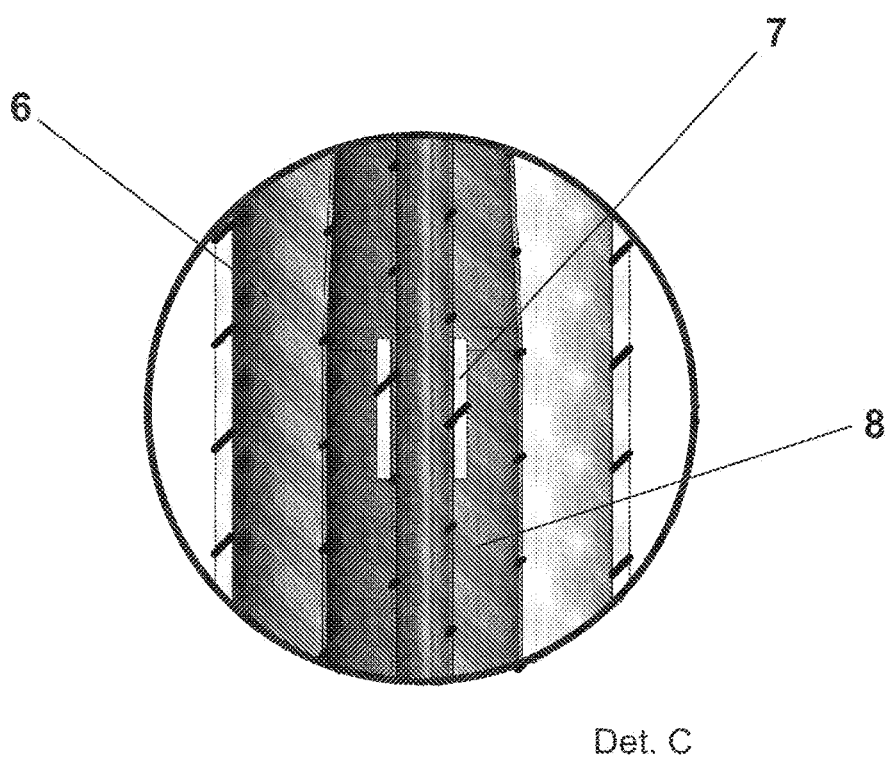
FIG. 8: detail C indicated in FIG. 4.
Figure 9:
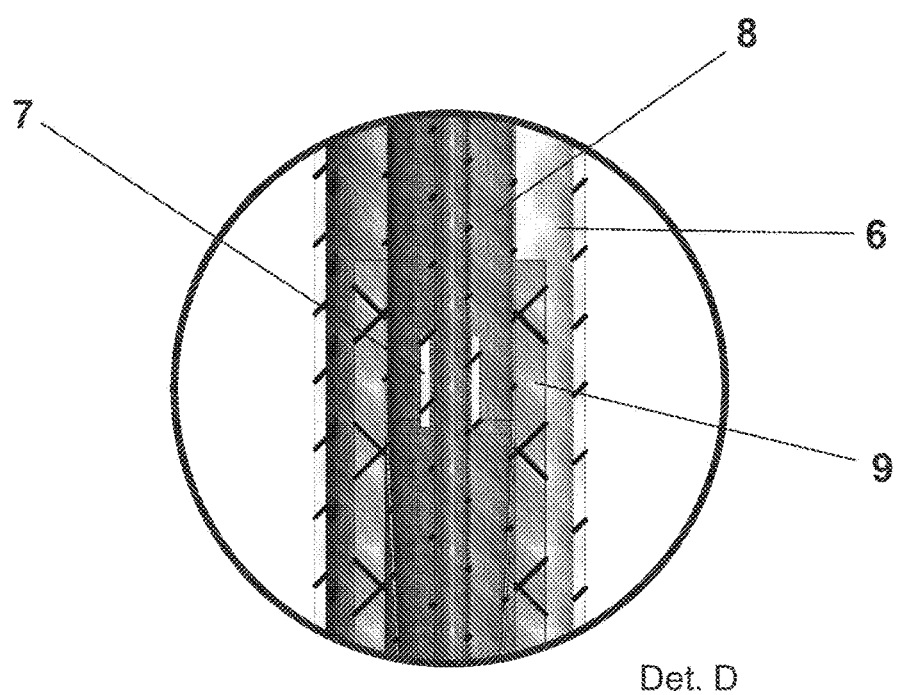
FIG. 9: detail D indicated in FIG. 4.
Figure 10:
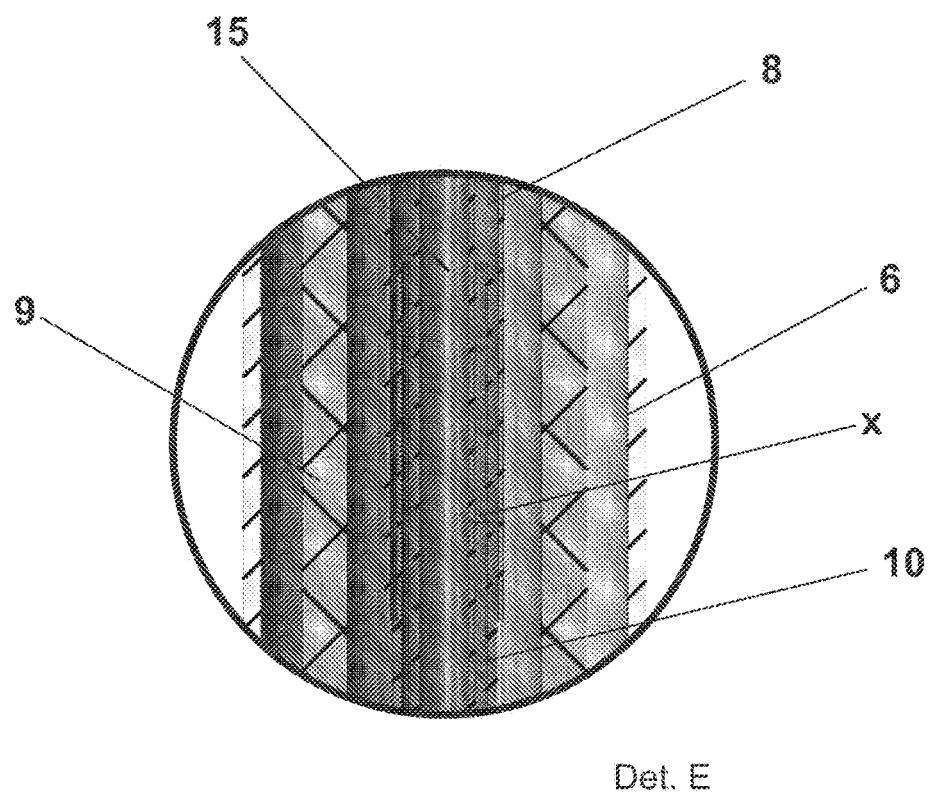
FIG. 10: detail E indicated in FIG. 4.
Figure 11:
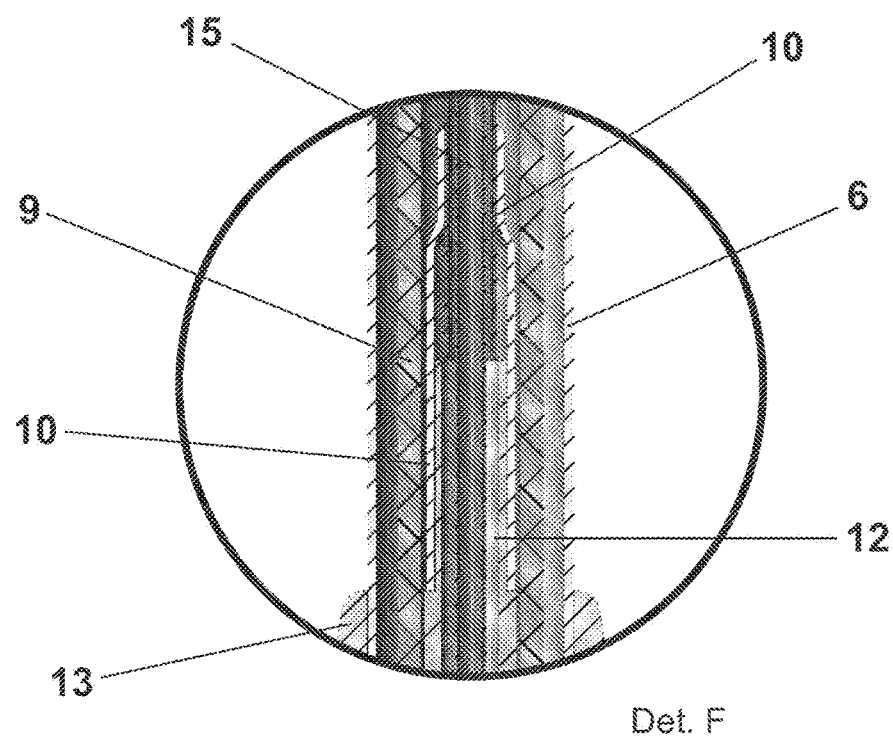
FIG. 11: detail F indicated in FIG. 4.
Figure 12:
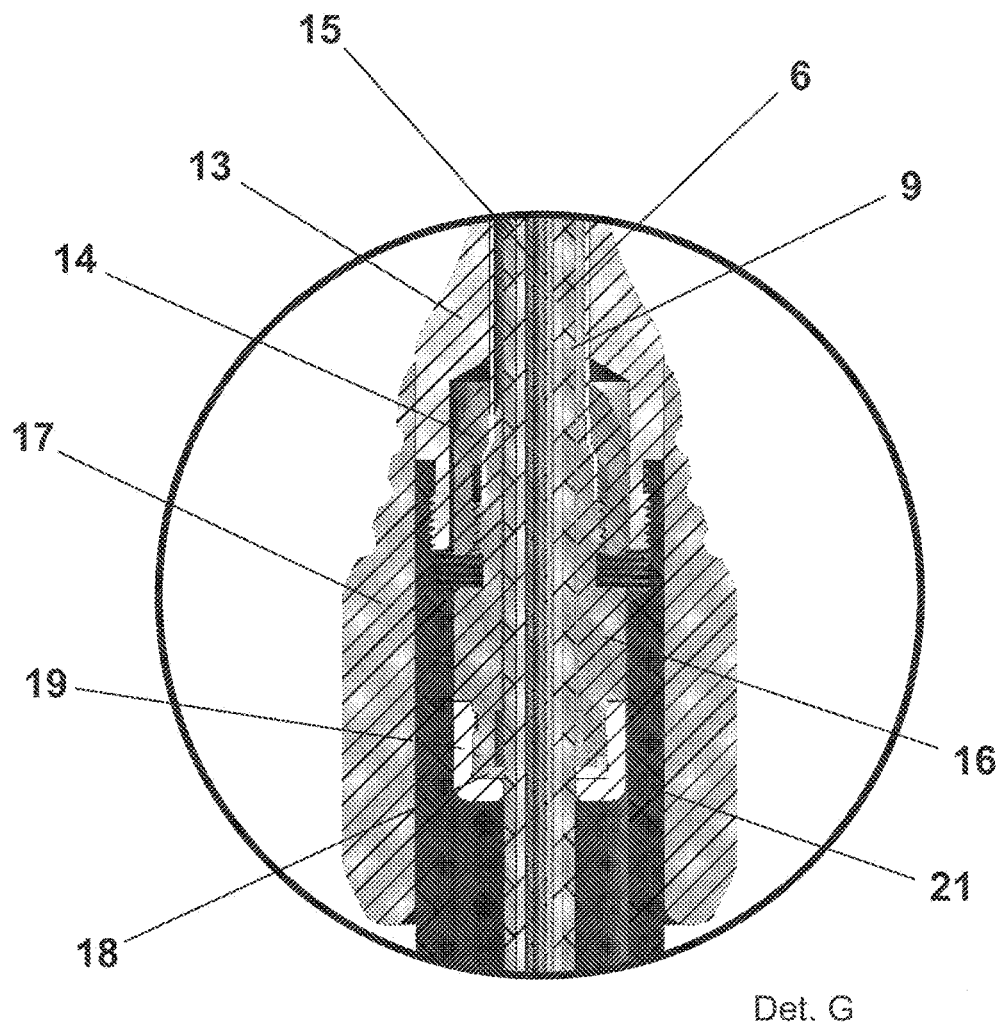
FIG. 12: detail G indicated in FIG. 4.
Figure 13:
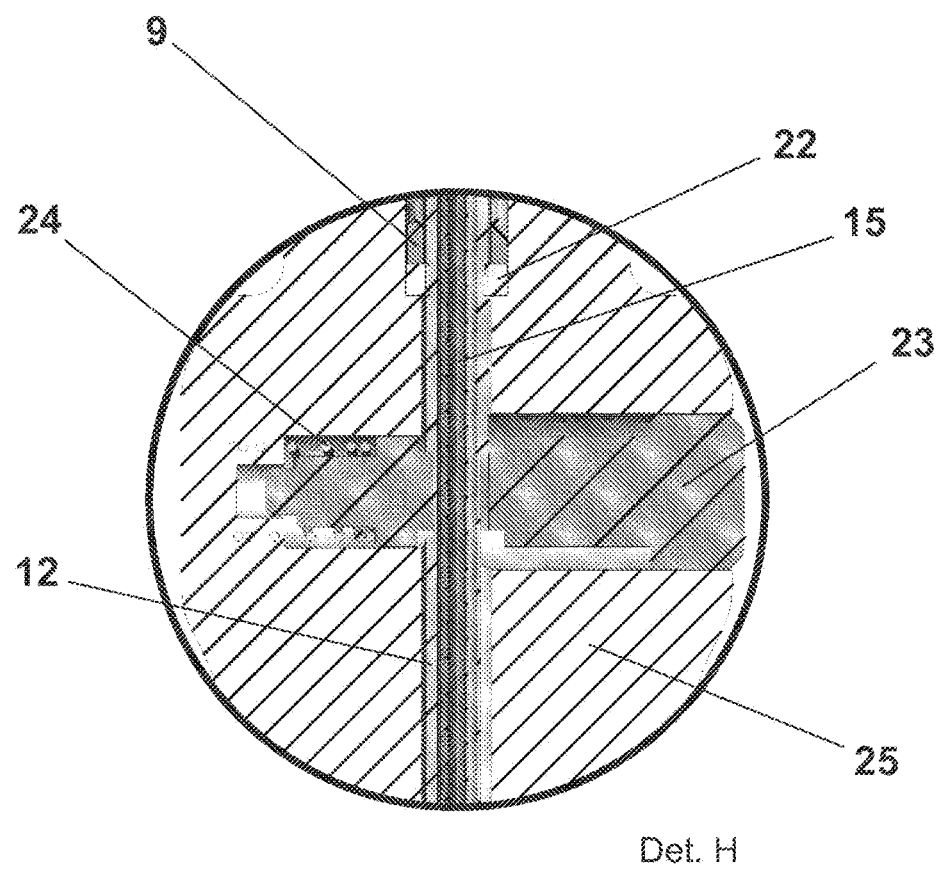
FIG. 13: detail H indicated in FIG. 4.
Figure 14:
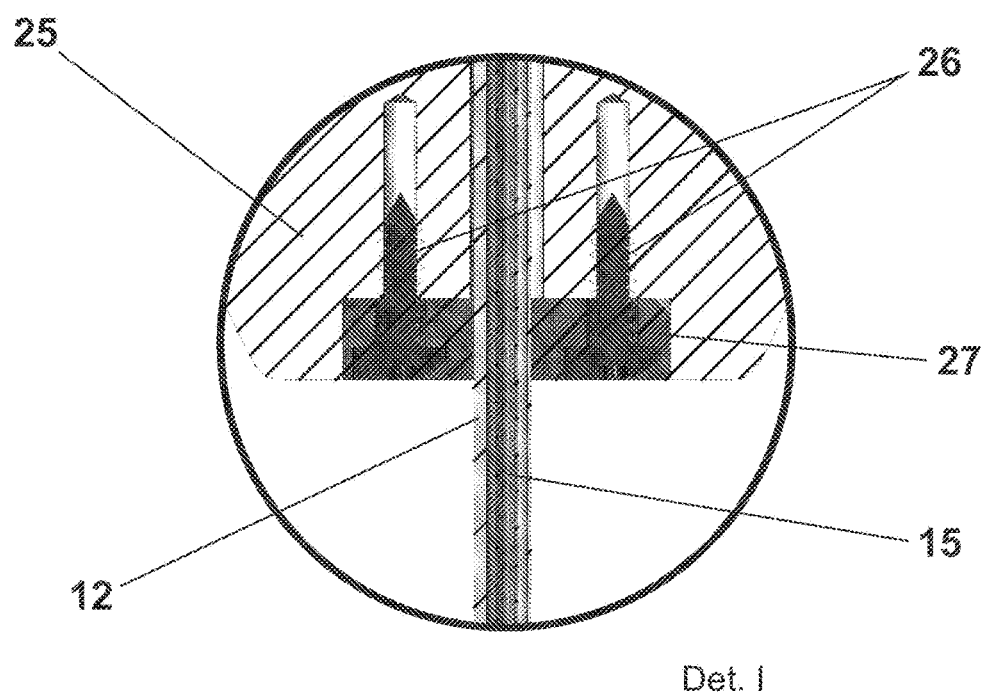
FIG. 14: detail I indicated in FIG. 4.
Figure 15:
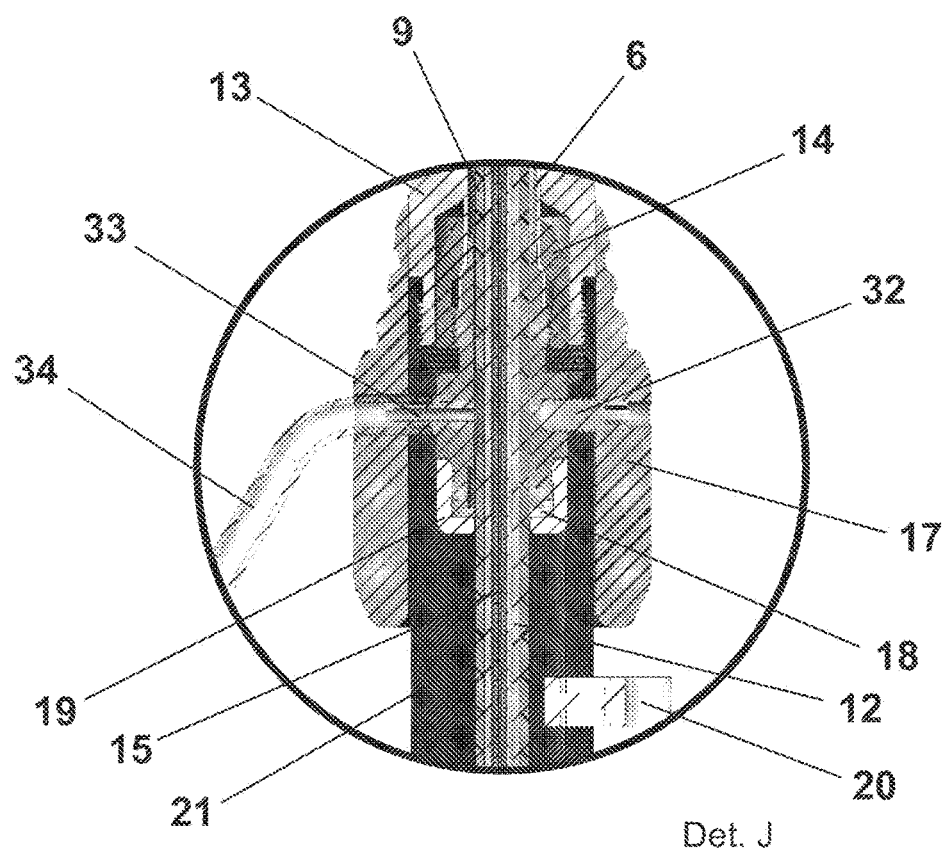
FIG. 15: detail J indicated in FIG. 5.
Figure 16:
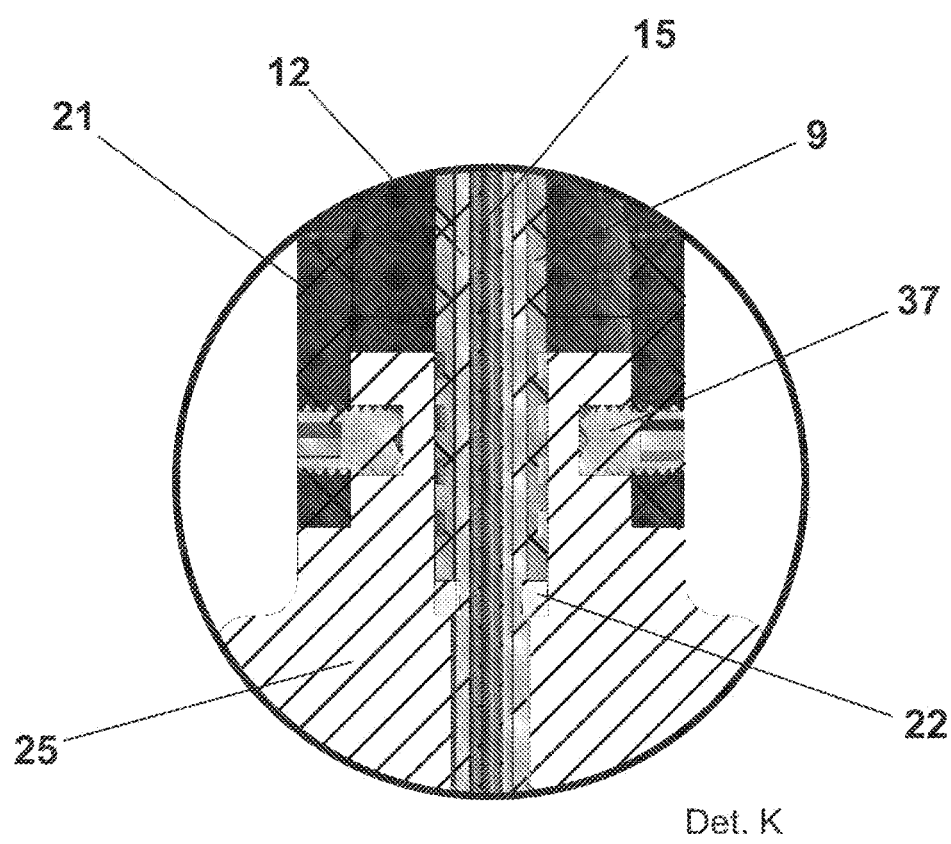
FIG. 16: detail K indicated in FIG. 5.
Figure 17:
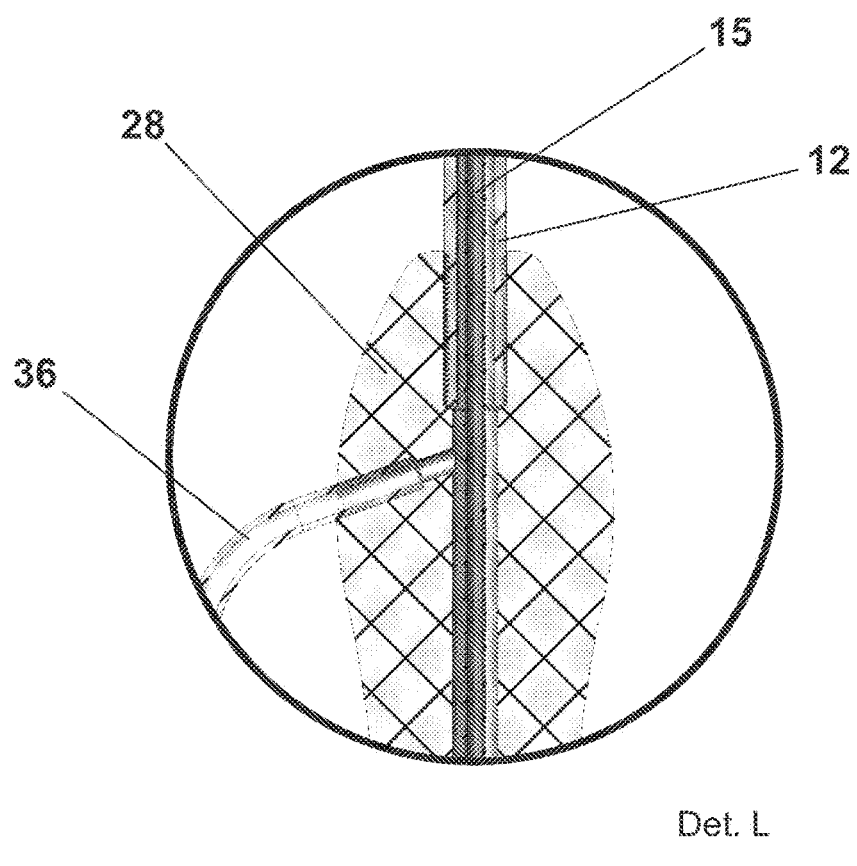
FIG. 17: detail L indicated in FIG. 5.
Figure 18:
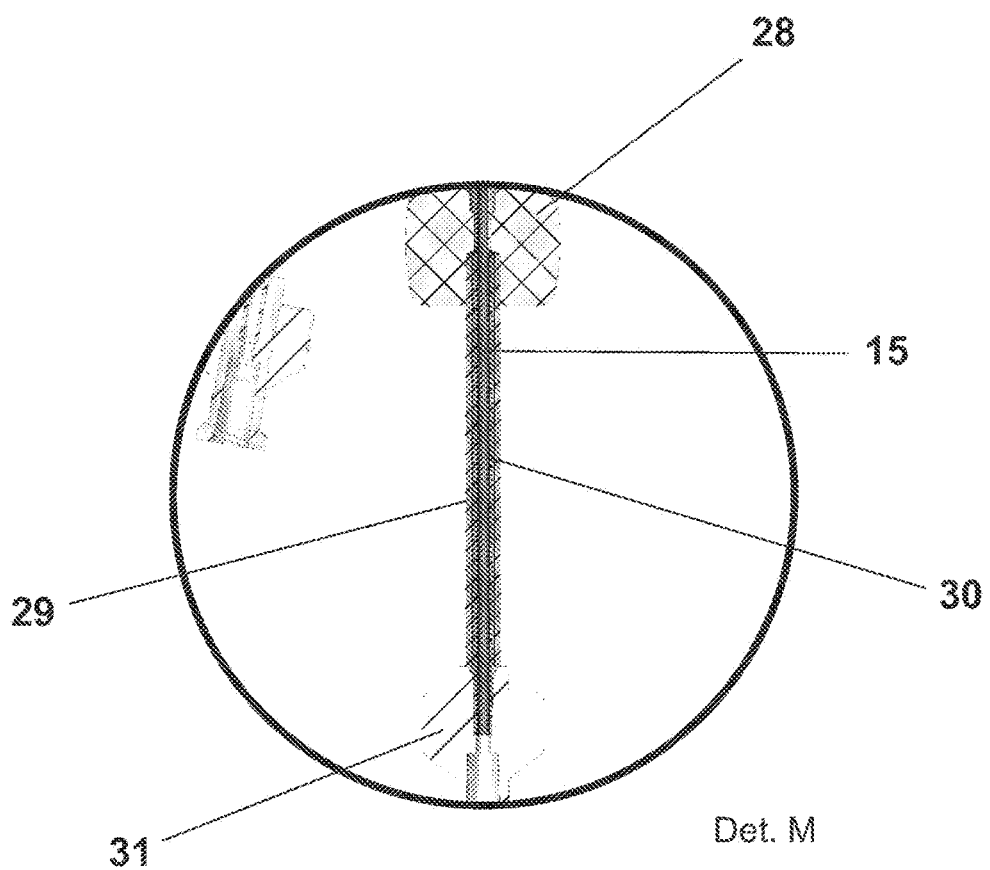
FIG. 18: detail M indicated in FIG. 5.
Figure 19:
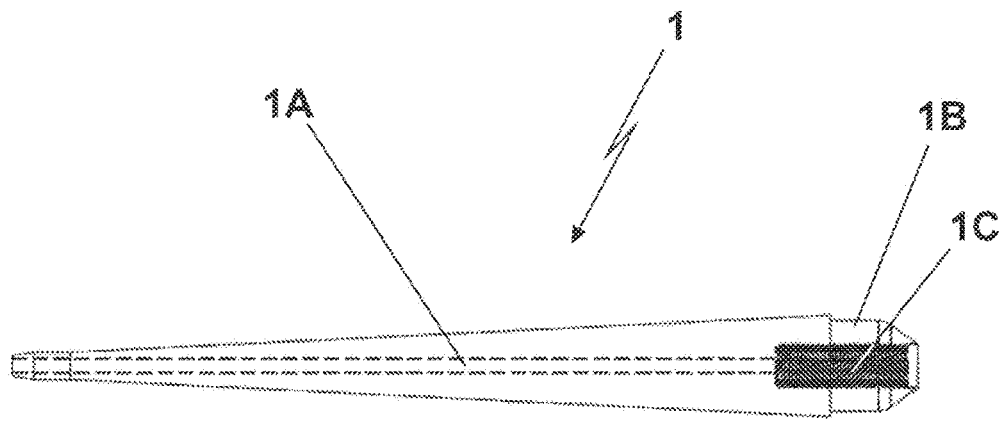
FIG. 19: a side view of the tip.
Figure 20:
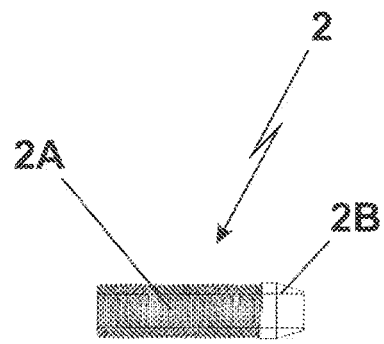
FIG. 20: a side view of the locking thread.
Figure 21:
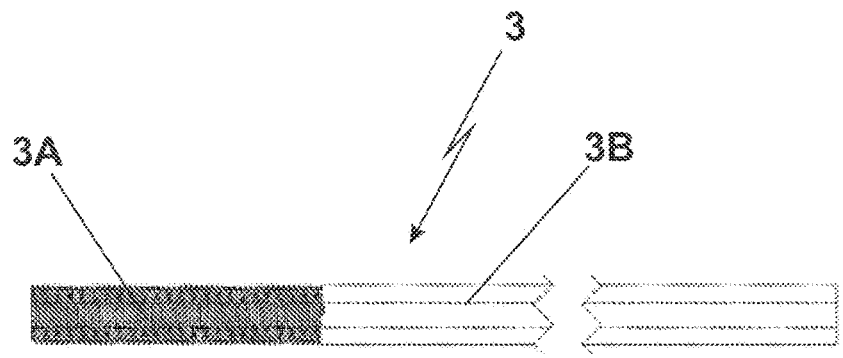
FIG. 21: a side view of the main tube.
Figure 22:
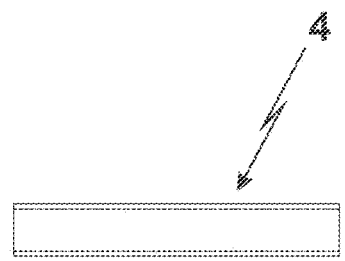
FIG. 22: a side view of the junction.
Figure 23:
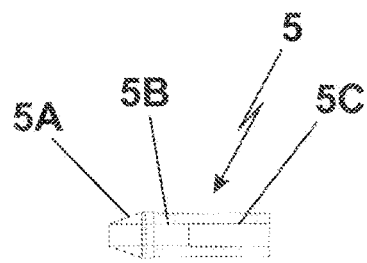
FIG. 23: a side view of the tip of the balloon.
Figure 24:
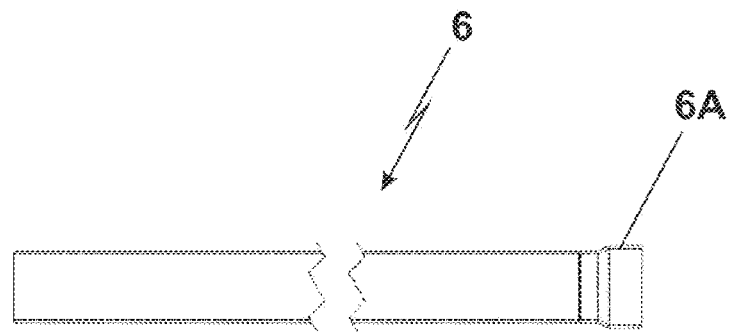
FIG. 24: a side view of the sheath tube.
Figure 25:
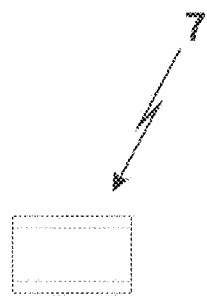
FIG. 25: a side view of the proximal radio-opaque marking.
Figure 26:
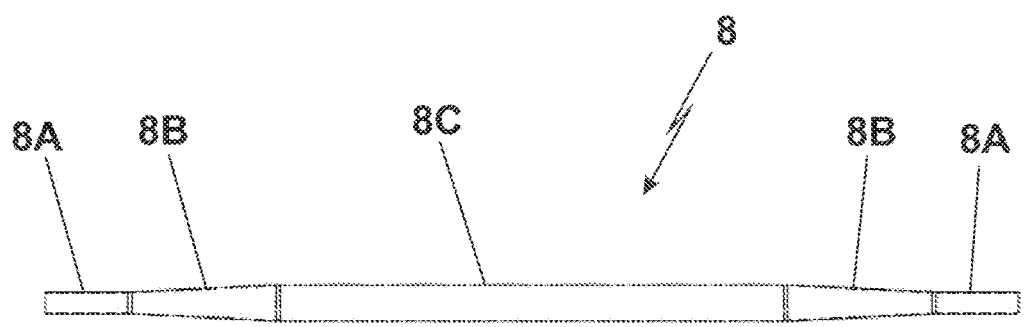
FIG. 26: a side view of the balloon.
Figure 27:
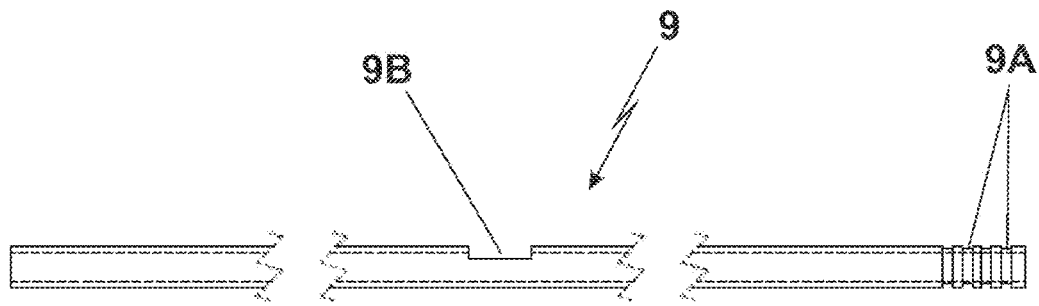
FIG. 27: a side view of the bearing tube.
Figure 28:
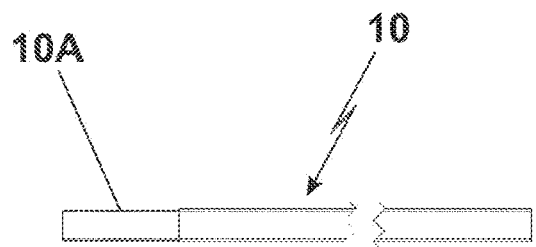
FIG. 28: a side view of the sheath tube balloon.
Figure 29:
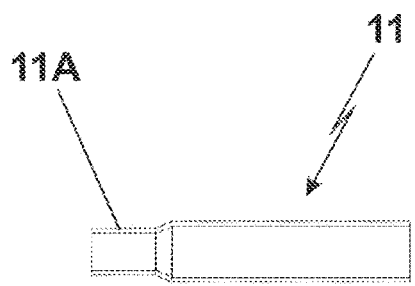
FIG. 29: a side view of the second junction.
Figure 30:
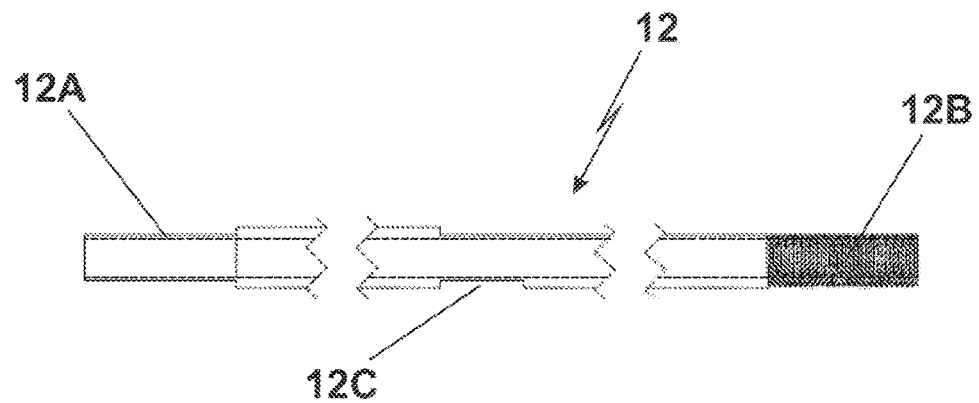
FIG. 30: a side view of the rod.
Figure 31:
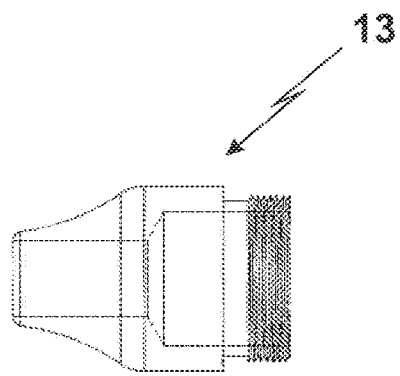
FIG. 31: a side view of the tip of the bar.
Figure 32:
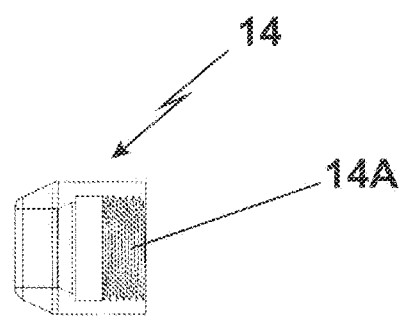
FIG. 32: a side view of the sheath housing nut.
Figure 33:
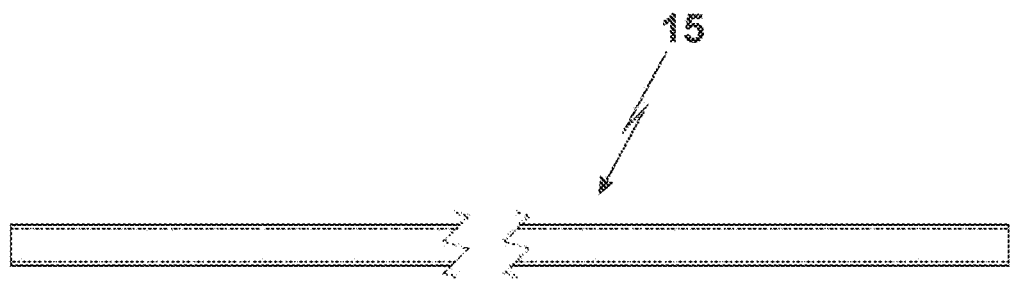
FIG. 33: a side view of the microlumen tube.
Figure 34:
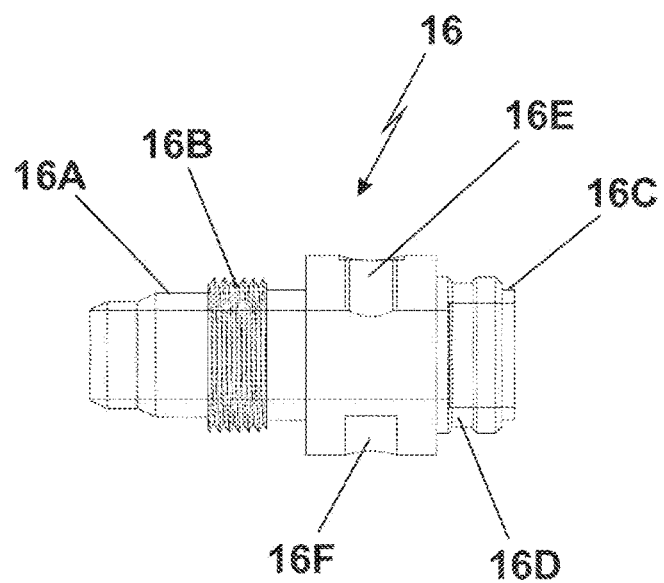
FIG. 34: a side view of the housing.
Figure 35:
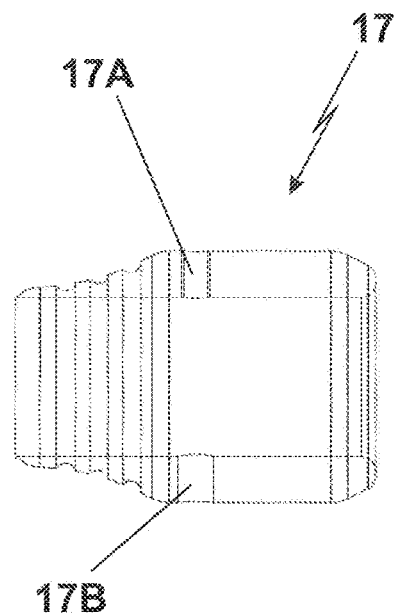
FIG. 35: a side view of the pulling ring.
Figure 36:
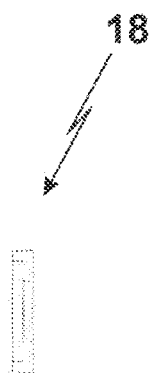
FIG. 36: a side view of the retention valve.
Figure 37:
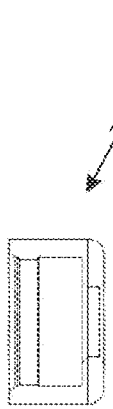
FIG. 37: a side view of the nut valve.
Figure 38:
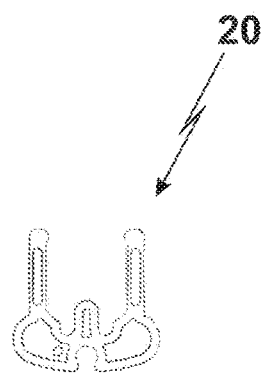
FIG. 38: a side view of the bar lock.
Figure 39:
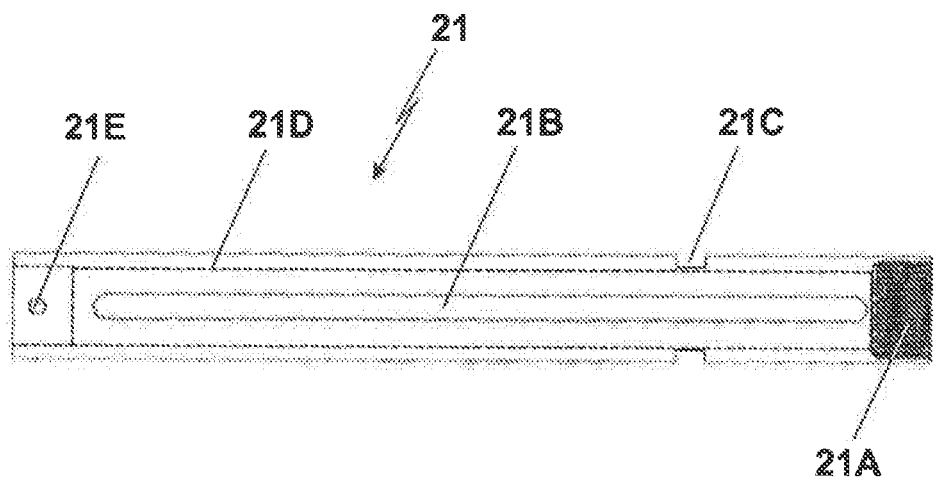
FIG. 39: a side view of the intermediate bar.
Figure 40:
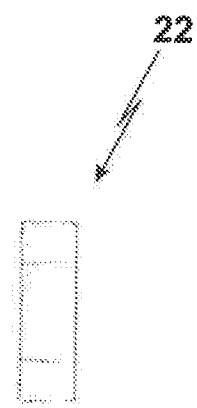
FIG. 40: a side view of the valve.
Figure 45:
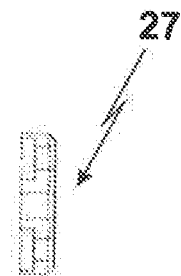
FIG. 45: a side view of the rod lock.
Figure 46:
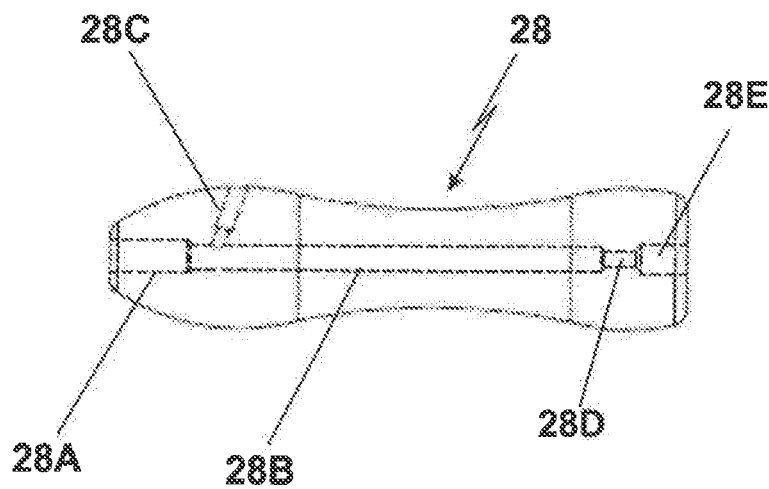
FIG. 46: a side view of the crank.
Figure 47:
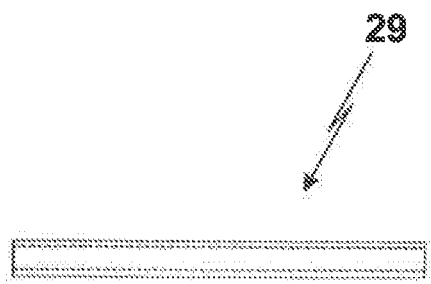
FIG. 47: a side view of the extension tube.
Figure 48:
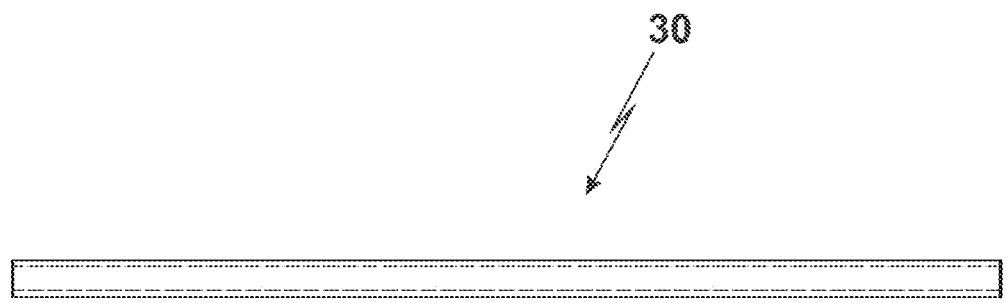
FIG. 48: a side view of the second extension tube.
Figure 49:
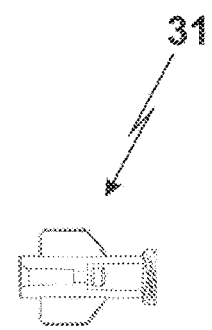
FIG. 49: a side view of the cover.
Figure 50:
FIG. 50: a side view of the headless screw.
Figure 51:
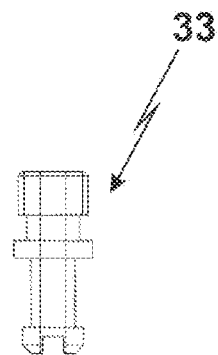
FIG. 51: a side view of the connector.
Figure 52:
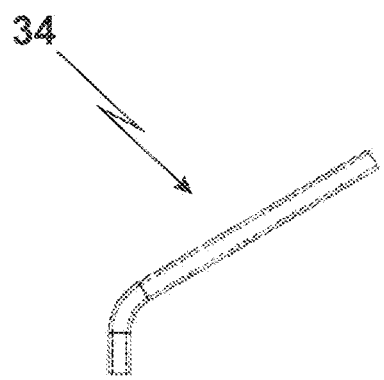
FIG. 52: a side view of the curved extension tube.
Figure 53:
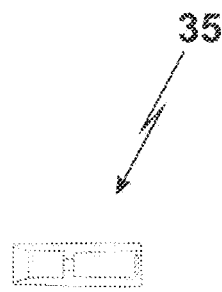
FIG. 53: a side view of the Female Luer Adapter—FLA.
Figure 54:
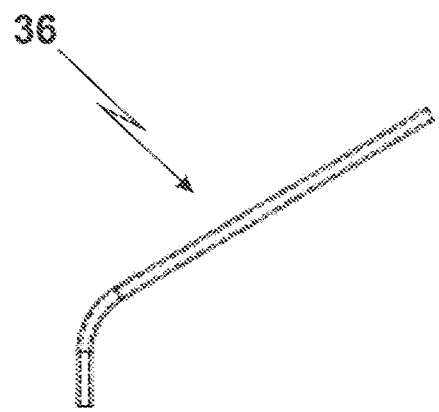
FIG. 54: a side view of the second curved extension tube.

According to FIGS. 1 to 54, the device is formed by a truncated cone body tip (1) which non-traumatic and flexible so that it can be adapted to tortuousness, provided with a through-hole (1A), at the inner end of an undercut (1B) and inside a housing (1C) having an inner thread, attached to which is a cylindrical lock (2) provided with an outer thread (2A) and a through-hole (2B) having an inner thread for attaching the main tube (3) provided with a thread (3A) at one of its ends and a through-hole (3B), and attached to the undercut (1C) of the tip (1) is the end of the sheath tube (6) that is provided with an annular shoulder (6A) at the opposite end thereof and made of a biocompatible plastic polymer, preferably polyacetal and polytetrafluorethylene, and coated with a hydrophilic polymer that makes it easy to slide same. Optionally, the sheath tube (6) can be twisted in order to provide same with higher resistance.

Attached to the opposite end of the main tube (3) is a tubular junction (4) inside which is attached the tip (5) of the balloon, provided with an annular shoulder having a bevel (5A) at one of its ends and an inner through-hole, a lower diameter portion (5B) and a higher diameter portion (5C), the latter being coupled to the end of a tubular microlumen (15), and on same and under the end of the junction (4) is attached the balloon (8) that is provided with a tubular portion (8A) at the ends thereof, followed by a truncated cone portion (8B) and a higher diameter tubular portion (8C) in the center region. Proximal radio-opaque markings (7) preferably made of barium sulfate and titanium dioxide so that they can be viewed easily during the procedure and the hydrophilic coating are provided on the microlumen (15) in the direction of the end of the truncated cone portions (8B) to indicate the tubular portion (8C). Said balloon (8) is preferably made of ethylene polyterephthalate.

At the opposite end of the balloon (8), the lower diameter end (10A) of the sheath tube of the balloon (10) is inserted at a distance "x" from the microlumen (15), inside which the fluid flows to expand the balloon (8), and coupled to the region close to the proximal radio-opaque marking (7) is the smooth end of the bearing tube (9) that lies under the sheath tube (6) and is provided with annular channels at the opposite end and a slit (9B) in the center thereof.

Attached to the other end of said sheath tube of the balloon (10) is the lower diameter portion (11A) of the junction (11) that receives the other end the smooth lower diameter region (12A) of the tubular rod (12) that is also provided with a lower diameter threaded region (12B) and a channel (12C) in the center thereof and is kept under the bearing tube (9) and under a part of the sheath tube (6) that is housed with its annular shoulder (6A) fit into the end (16A) of the housing (16) and fixed by a nut (14) through the inner threaded region (14A) thereof that is screwed to the thread (16B) of the housing (16) that is provided with an undercut at the opposite end (16C) thereof for fitting the annular retaining valve (18) that is locked by the valve nut (19) coupled to the channel (16D). Said housing (16) is wrapped by the end of the intermediate bar (21) provided with an inner thread (21A) to which the tip of the bar (13) with a through-hole is threaded and a housing that wraps the nut (14), and the assembly is wrapped by the pulling ring (17) fixed by the headless screw (32) that attaches the housing (16) and the pulling ring (17), respectively, through the threaded holes (16E) and (17A). On the opposite side, the hole (16F) is provided in the housing (16), the central slit (21B) is provided at the intermediate bar (21) and the hole (17B) is provided in the pulling ring (17), all of which are coincident, into which are inserted the connector (33) and the curved expanding tube (34) that is provided at the end thereof with a Female Luer Adapter-FLA (35) to which is coupled the syringe that injects the liquid for washing the device.

Said intermediate bar (21) is also provided with a channel (21C) to fit the lock (27) that limits the movement of the pulling ring (17), a through-hole (21D) across the lumen (15), the rod (12) and the bearing tube (9) pass and whose end is provided with holes (21E) that match the holes (25A) provided in the portion of the handle (25) for attaching the intermediate bar (21) thereto through screws (37), which end is also provided with teeth (25B) that fit into the channels (9A) of the bearing tube (9) that is fixed at the end of the handle (25) which is provided with a fluid retaining valve (22), and provided with a through-hole across the microlumen (15) and the rod (12) pass, and provided in the opposite end with holes (25C) for attaching the handle (25) to the intermediate bar (21) through screws (26), and the handle (25) is also provided with a housing (25D) for the locking rod (27), and the top front portion (25E) is provided with a hole (25F) for coupling the pressure spring (24) and a locking pin (23) that keeps the rod (12) locked through the channel (12C) provided therein. Said handle (25) is made of a biocompatible plastic polymer, preferably polyacetal and polytetrafluorethylene.

Said rod (12) extends to the crank (28), where it is attached through the threads (12B) to the higher diameter hole (28A) that extends to the lower diameter hole (28B) across the microlumen (15) passes and wherein is provided an oblique hole (28C) attached to which is the expanding tube (36) provided at its end with a valve (31) for coupling the syringe that injects the liquid to expand the balloon (8). Said hole (28B) is provided with a throat (28D) that forms a housing (28E) for coupling the expanding tube (29) and the tube (30) across the microlumen (15) passes, and they both fit into the sealing cover (31) of the through-hole of the microlumen (15) across the guide wire passes at the time of the surgery.

Figure 55:
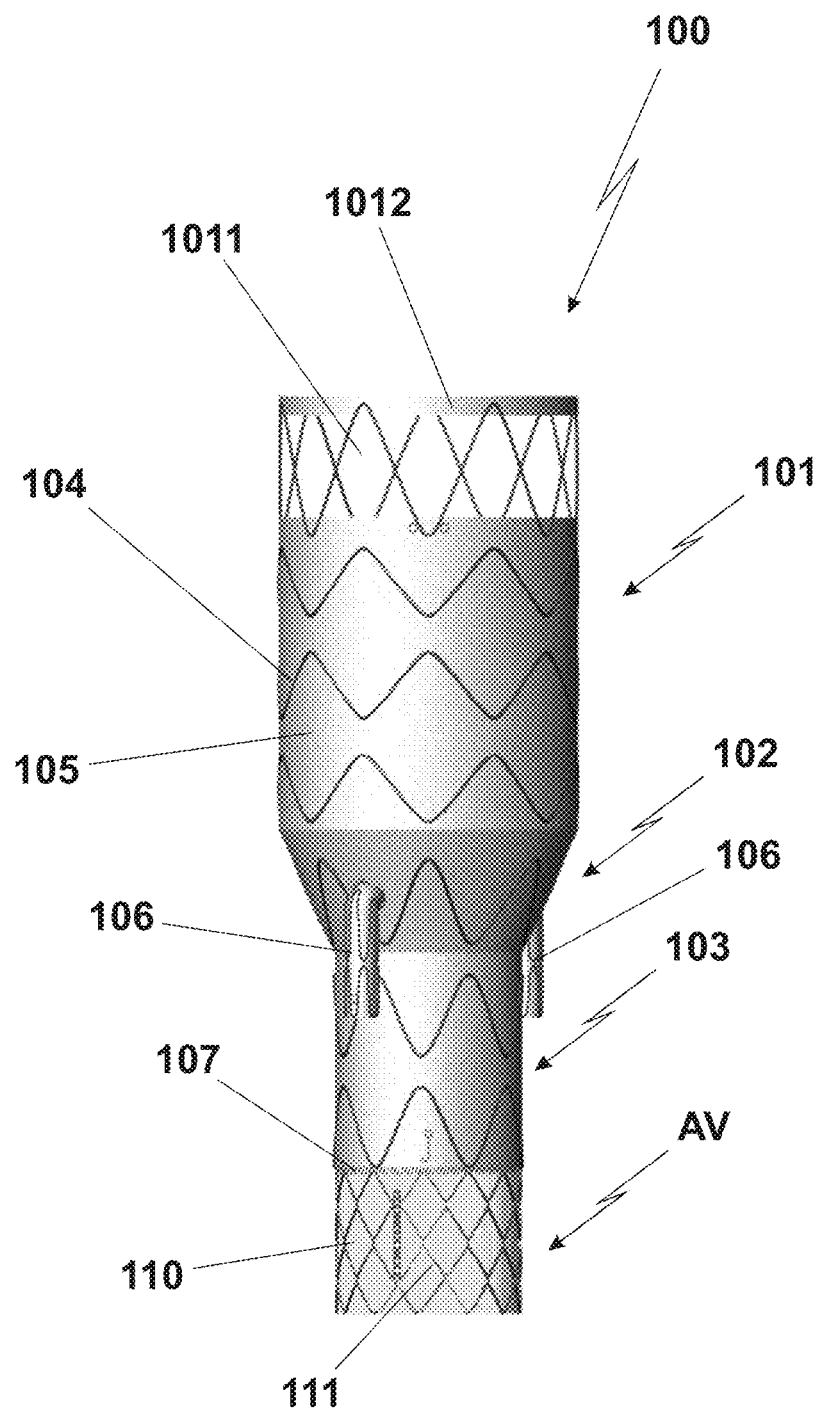
FIG. 55: a side view of the valved endoprosthesis.

According to FIG. 55, the valved endoprosthesis comprises the expandable tubular body (100) provided with a distal higher diameter region (101) followed by a bevel (102), and a proximal lower diameter region (103) formed by a metallic structure (104) coated with a fabric (105) that extends from the distal edge to the proximal edge of the region (103), where is provided the suture (107) of the aortic valve (AV) through the coating (110) that extends to the upper edge thereof on the metallic structure (111) having a hinge that allows same to be compressed and, when in use, expanded through the action of the balloon (8), or self-expanded. In the region of the bevel (102) are provided branches (106) or vents that can be external or internal and located between 1 and 2 branches. Said tubular body (100) is made of a biocompatible metallic alloy that is coated with an outer tubular low porosity membrane provided with proximal and distal radio-opaque markings.

Optionally, the valved endoprosthesis can have a single metallic structure for the tubular body (100) and the aortic valve (AV), so that the latter will not need to be expanded by the balloon (8), and it can be automatically extended as it is uncapsulated.

Still optionally, the distal region (101) can be provided with an uncoated area (1011) at its edge to facilitate the attachment thereof, known as free-flow, and a strip preferably made of a polyester fabric (1012) covering the outer edge that can vary according to the anatomy of the patient.

Realization of the Invention

The object of the present patent is to correct ascending aorta related diseases and replace the aortic valve through endovascular access in patients suffering from calcified aortic valve stenosis where the conventional surgery is contraindicated because of the high surgical risk and the associated ascending aorta disease that requires treatment.

With the valved endoprosthesis releasing device and the valved endoprosthesis conceived herein, the invention comprises a valved endoprosthesis releasing device and a valved endoprosthesis fully coated to isolate the blood flow from the sick ascending aorta region, such as aneurism or dissection. However, the ascending aorta branches, right and left coronaries, need to be preserved. To that end, branches (106) or vents are provided whose function is to preserve the flow of said arteries. The branches or vents of the prosthesis will be connected to the coronary arteries through coated stents.

The releasing device facilitates the implantation of the valved endoprosthesis by means of an endovascular surgical procedure. The device has a not fully compliant balloon (8) connected thereto, whose purpose is to expand the aortic valve (AV).

To compress the aortic valve (AV) on the balloon (8), a conventional crimping device is used in parallel. This device contains a handle, a compression area and a support base. The compression is caused by the movement of the handle which actuates the compression crimping mechanism and reduces the diameter of the interior of the device.

For the preparation and use of the invention, the valved endoprosthesis should be removed from its package and inserted in a container containing a physiological saline solution, washed exhaustively to remove the biological material preserving solution, and the crimping mechanism should be removed from its package and placed on a steady surface, as well as the releasing device. The balloon (8) of the releasing device is conveyed to the interior of the aortic valve (AV) of the valved endoprosthesis, in such a way that is located in the center of the radio-opaques markings (7) of the balloon (8). After being positioned, the whole assembly is introduced in the crimping mechanism to compress the aortic valve (AV) so that its diameter is reduced evenly. After the aortic valve (AV) is crimped, the tubular body (100) should be manually compressed in such a way that it is fully encapsulated in the sheath tube (6) of the releasing device.

After being correctly prepared, the releasing device with the valved endoprosthesis encapsulated therein should be inserted by the previously positioned rigid guide wire, always under radioscopic monitoring until the implant is suitably positioned.

The aortic valve (AV) should be located under the native ring, the correct position of which is when the middle portion of the aortic valve (AV) is on said ring. The use of transesofagic echocardiography to control the positioning simultaneously with the use of radioscopy is recommended.

After the correct positioning, the patient should be placed in a hipotense condition and then the lock is removed from the base (20) and the body (100) of the valved endoprosthesis starts being released by moving the pulling ring (17) until the whole body (100) is released or the pulling ring (17) reaches the end of the course of the intermediate bar (21), and then the locking pin (23) is pressed to release the tubular rod (12), allowing same to push the crank (28) until it touches the handle (25), and then the non-compliant balloon (8) should be inflated by injecting the solution through the expanding tube (36) until it reaches its working volume and pressure.

After the aortic valve (AV) of the valved endoprosthesis dilates, the balloon (8) is emptied and the releasing device is removed. It is necessary to check whether the valved endoprosthesis is functioning correctly and whether it is free of any leak. In the event of any leak, the balloon (8) can be used again to adjust the valved endoprosthesis. The releasing device should be removed and the incisions closed.

Advantages of the Invention

The valved endoprosthesis releasing device and the valved endoprosthesis thus obtained provide the following advantages:

They make it possible to treat patients to whom the Bentall De Bono surgical procedure is counterindicated and would not suffer any intervention related to their disease;

They allow for a minimally invasive access, wherein the flow is kept without clamping[11];

The device provides a lower blood transfusion rate, a shorter internment time, a shorter time in the intensive care unity, and lower costs[12];

The device can release the valved endoprosthesis in a suitable way, making it possible to insuflate the aortic valve (AV) whenever it is so required;

Possibility of treating the coronaries during the same procedure and without any damage to the patient;

Possibility of treating extensive ascending aorta diseases, such as aneurisms and dissections; and It is possible to develop the valved endoprosthesis in several lengths, diameters and conformations, and adapt same to the anatomy of each patient.

The scope of the present patent shall not be limited to the constructive details, but to the terms defined in the claims and its equivalents.

REFERENCES

The following citations have been made:
1.—Albuquerque L C, Palma J H, Braile D M, Gomes W. Diretrizes para a Cirurgia das Doenengas da Aorta. Arq Bras Cardiol. 2004; 82(supl V):35-50;
2.—Bentall H, De Bono A. A technique for complete replacement of the ascending aorta. Thorax. 1968; 23(4): 338-9;
3.—Ingrund J C, Nasser F, Jesus-Silva S G, et al. Tratamento hibrido das doenengas complexas da aorta torAcica. Rev Bras Cir Cardiovasc. 2010; 25(3):303-10;
4.—Umaña J P, Miller D C, Mitchell R S. What is the best treatment for patients with acute type B aortic dissections: Medical, surgical, or endovascular stent-grafting? Ann Thorac Surg. 2002; 74(5):S1840-3;
5.—Matalanis G, Durairaj M, Brooks M. A hybrid technique of aortic arch transposition and antegrade stent graft deployment for complete arch repair without cardiopulmonary bypass. Eur J Cardiothorac Surg. 2006; 29:611-2;
6.—Pires A C, Saporito W F, Ramos Filho R A, Castelo Jr H J, Almeida D R. Cirurgia de Bentall—De Bono associada a revascularizagao direta do miocArdio: relato de caso. Rev Bras Cir Cardiovasc 1997; 12 (4): 387-91;
7.—Svensson L G, Crawford E S, Hess K R, Coselli J S, Safi H J. Composite valve graft replacement of the proximal aorta: comparison of the arts in 348 patients. Ann Thorac Surg. 1992; 54(3):427-37;
8.—Asano K I, Ando T, Hanada S, Maruyama Y. Control of bleeding during the Bentall operation. J Cardiovasc Surg (Torino). 1983; 24(1):13-4;
9.—Cabrol C, Pavie A, Mesnildrey P, Gandjbakhch I, Laughlin L, Bors V, et al. Long-term results with total replacement of the ascending aorta and reimplantation of the coronary arteries. J Thorac Cardiovasc Surg. 1986; 91(1):17-25;
10.—Morales J P, Taylor P R, Bell R E, Chan Y C, Sabharwal T, Carrell T W, et al. Neurological complications following endoluminal repair of thoracic aortic disease. Cardiovasc Intervent Radiol. 2007; 30(5):833-9;
11.—Dake M D, Kato N, Mitchell R S, et al. Endovascular stent-graft placement for the treatment of acute aortic dissection. N Engl J Med. 1999; 340:1546-52; and 12.—Palma J H, Buffolo E, Gaia D. Tratamento endovascular das doengas da aorta: Visao geral. Ver Bras Cir Cardiovasc. 2009; 24(2 Supl 1):40s-44s.

What is claimed is:

1. A valved endoprosthesis comprising:
an expandable tubular body having a unitary metallic structure for implantation into a patient, wherein the unitary metallic structure is composed of the following:
   a first metallic portion having:
      a distal higher diameter region,
      a proximal lower diameter region,
      a suture of an aortic valve provided in the lower diameter proximal region,
      a bevel that inseparably connects the distal and the proximal regions, and
      a plurality of external or internal branches or vents in a region of the bevel, wherein the first metallic portion is coated with a fabric extending from the distal region to the proximal region via the bevel; and
   a second metallic portion attached to the first metallic portion in a non-overlapping manner following implantation and having a hinge that allows the second metallic portion to be compressed, and when in use, expanded through an action of a balloon or by self-expansion;
   wherein the suture of the aortic valve is provided through a coating that extends to an upper edge of the second metallic portion; and
   wherein the expandable tubular body is made of a biocompatible metallic alloy with proximal and distal radio-opaque markings.

2. The valved endoprosthesis according to claim 1, wherein the biocompatible metallic alloy of the tubular body is nitinol and cobalt-chromium.

3. The valved endoprosthesis according to claim 1, wherein the aortic valve is expanded automatically as the valved endoprosthesis is uncapsulated.

4. The valved endoprosthesis according to claim 1, wherein the distal region is provided with an uncoated area at an edge to facilitate attachment, and a strip made of a polyester fabric covering an outer edge of the uncoated area that varies according to an anatomy of a patient.

* * * * *